US012076147B2

(12) United States Patent
Trissel

(10) Patent No.: US 12,076,147 B2
(45) Date of Patent: *Sep. 3, 2024

(54) LANCING DEVICE WITH SIDE ACTIVATED CHARGE AND EJECT MECHANISMS

(71) Applicant: FACET TECHNOLOGIES, LLC, Atlanta, GA (US)

(72) Inventor: John A. Trissel, Canton, GA (US)

(73) Assignee: FACET TECHNOLOGIES, LLC, Atlanta, GA (US)

(*) Notice: Subject to any disclaimer, the term of this patent is extended or adjusted under 35 U.S.C. 154(b) by 1036 days.

This patent is subject to a terminal disclaimer.

(21) Appl. No.: 16/551,237

(22) Filed: Aug. 26, 2019

(65) Prior Publication Data

US 2019/0374143 A1 Dec. 12, 2019

Related U.S. Application Data

(62) Division of application No. 13/860,270, filed on Apr. 10, 2013, now Pat. No. 10,456,069.

(Continued)

(51) Int. Cl.
*A61B 5/151* (2006.01)
*A61B 5/15* (2006.01)

(52) U.S. Cl.
CPC .... *A61B 5/15115* (2013.01); *A61B 5/150022* (2013.01); *A61B 5/150198* (2013.01); *A61B 5/15113* (2013.01); *A61B 5/15117* (2013.01); *A61B 5/1519* (2013.01); *A61B 5/15194* (2013.01); *A61B 5/150412* (2013.01); *A61B 5/150503* (2013.01); *A61B 5/150816* (2013.01); *A61B 5/1513* (2013.01)

(58) Field of Classification Search
CPC .......... A61B 5/15115; A61B 5/150022; A61B 5/150198; A61B 5/15113; A61B 5/15117; A61B 5/1519; A61B 5/15194; A61B 5/150412; A61B 5/150503; A61B 5/150816; A61B 5/1513
See application file for complete search history.

(56) References Cited

U.S. PATENT DOCUMENTS

| 4,442,836 A | 4/1984 | Meinecke et al. |
| 4,527,561 A | 7/1985 | Burns |

(Continued)

FOREIGN PATENT DOCUMENTS

| EP | 1090584 A2 | 4/2001 |
| WO | 2007108967 A2 | 9/2007 |
| WO | 2010019741 A1 | 2/2010 |

OTHER PUBLICATIONS

International Search Report & Written Opinion for PCT/US2013/035974; Sep. 6, 2013; 15 pgs.

*Primary Examiner* — Sarah W Aleman
*Assistant Examiner* — Rachel S Highland
(74) *Attorney, Agent, or Firm* — Perilla Knox & Hildebrandt LLP; Stephanie L. Davy-Jow; Bradley Groff

(57) ABSTRACT

A lancing device having a housing with a proximal end, a distal end and a longitudinal axis. The lancing device also has a lancet carrier translationally supported with respect to the housing. The lancet carrier has a proximal end and a distal end. The lancing device additionally has a charging mechanism and/or an ejection mechanism adapted to pivot into the lancing device for engaging portions of the lancet carrier to perform the same.

10 Claims, 11 Drawing Sheets

Related U.S. Application Data

(60) Provisional application No. 61/623,276, filed on Apr. 12, 2012.

(56) References Cited

U.S. PATENT DOCUMENTS

| | | | |
|---|---|---|---|
| 4,539,988 A | 9/1985 | Shirley et al. | |
| 4,628,929 A | 12/1986 | Intengan et al. | |
| 4,892,097 A | 1/1990 | Ramalletta et al. | |
| 4,895,147 A | 1/1990 | Bodicky et al. | |
| 4,976,724 A | 12/1990 | Nieto et al. | |
| 5,133,730 A | 7/1992 | Biro et al. | |
| 5,196,025 A | 3/1993 | Ranalletta et al. | |
| 5,212,879 A | 5/1993 | Biro et al. | |
| 5,282,822 A | 2/1994 | Macors et al. | |
| 5,314,441 A | 5/1994 | Cusack et al. | |
| 5,318,583 A | 6/1994 | Rabenau et al. | |
| 5,318,584 A | 6/1994 | Lange et al. | |
| 5,423,847 A | 6/1995 | Strong et al. | |
| 5,464,418 A | 11/1995 | Schraga | |
| 5,518,006 A | 5/1996 | Mawhirt et al. | |
| 5,527,333 A | 6/1996 | Nikkels et al. | |
| 5,527,334 A | 6/1996 | Kanner et al. | |
| 5,529,581 A | 6/1996 | Cusack | |
| 5,554,166 A | 9/1996 | Lange et al. | |
| 5,613,978 A | 3/1997 | Harding | |
| 5,628,765 A | 5/1997 | Morita | |
| 5,730,753 A | 3/1998 | Morita | |
| RE35,803 E | 5/1998 | Lange et al. | |
| 5,797,940 A | 8/1998 | Mawhirt et al. | |
| 5,908,434 A | 6/1999 | Schraga | |
| 5,916,230 A | 6/1999 | Brenneman et al. | |
| 5,984,940 A | 11/1999 | Davis et al. | |
| 6,022,366 A | 2/2000 | Schraga | |
| 6,042,595 A | 3/2000 | Morita | |
| 6,045,567 A | 4/2000 | Taylor et al. | |
| 6,156,050 A | 12/2000 | Davis et al. | |
| 6,156,051 A | 12/2000 | Schraga | |
| 6,168,606 B1 | 1/2001 | Levin et al. | |
| 6,190,398 B1 | 2/2001 | Schraga | |
| 6,197,040 B1 | 3/2001 | LeVaughn et al. | |
| 6,221,089 B1 | 4/2001 | Mawhirt | |
| 6,283,982 B1 | 9/2001 | LeVaughn et al. | |
| 6,322,575 B1 | 11/2001 | Schraga | |
| 6,332,871 B1 | 12/2001 | Douglas et al. | |
| 6,409,740 B1 | 6/2002 | Kuhr et al. | |
| 6,419,661 B1 | 7/2002 | Kuhr et al. | |
| 6,451,040 B1 | 9/2002 | Purcell | |
| 6,514,270 B1 | 2/2003 | Schraga | |
| 6,530,937 B1 | 3/2003 | Schraga | |
| 6,558,402 B1 | 5/2003 | Chelak et al. | |
| 6,575,939 B1 | 6/2003 | Brunel | |
| 6,602,268 B2 | 8/2003 | Kuhr et al. | |
| 6,645,219 B2 | 11/2003 | Roe | |
| 6,749,618 B2 | 6/2004 | LeVaughn et al. | |
| 6,811,557 B2 | 11/2004 | Schraga | |
| 6,887,253 B2 | 5/2005 | Schraga | |
| 6,949,111 B2 | 9/2005 | Schraga | |
| 6,986,777 B2 | 1/2006 | Kim | |
| 7,105,006 B2 | 9/2006 | Shraga | |
| 7,160,313 B2 | 1/2007 | Galloway et al. | |
| 7,175,641 B1 | 2/2007 | Schraga | |
| 7,223,276 B2 | 5/2007 | List et al. | |
| 7,273,484 B2 | 9/2007 | Thoes et al. | |
| 7,288,102 B2 | 10/2007 | Griffin et al. | |
| 7,311,718 B2 | 12/2007 | Schraga | |
| 7,316,698 B1 | 1/2008 | Galloway et al. | |
| 7,322,998 B2 | 1/2008 | Kuhr et al. | |
| 7,452,365 B2 | 11/2008 | Galloway et al. | |
| 7,651,512 B2 | 1/2010 | Chelak et al. | |
| 7,655,019 B2 | 2/2010 | LeVaughn et al. | |
| 7,678,126 B2 | 3/2010 | Schraga | |
| 7,678,127 B2 | 3/2010 | Facet | |
| 7,682,318 B2 | 3/2010 | Alden et al. | |
| 7,842,060 B2 | 11/2010 | List | |
| 7,867,244 B2 | 1/2011 | Lathrop et al. | |
| 7,909,842 B2 | 3/2011 | Flynn et al. | |
| 7,914,547 B2 | 3/2011 | Curry et al. | |
| 7,947,057 B2 | 5/2011 | Schraga | |
| 7,955,348 B2 | 6/2011 | Trissel et al. | |
| 8,016,848 B2 | 9/2011 | Lathrop et al. | |
| 8,043,318 B2 | 10/2011 | Schraga | |
| 8,048,097 B2 | 11/2011 | Schraga | |
| 8,105,347 B2 | 1/2012 | Schraga | |
| 8,152,740 B2 | 4/2012 | Thoes et al. | |
| 8,211,036 B2 | 7/2012 | Schraga | |
| 8,257,380 B2 | 9/2012 | Schraga | |
| 8,303,615 B2 * | 11/2012 | Purcell | A61B 5/150618 606/181 |
| 8,357,107 B2 | 1/2013 | Draudt et al. | |
| 8,366,729 B2 | 2/2013 | LeVaughn et al. | |
| 8,398,664 B2 | 3/2013 | Lamps et al. | |
| 8,469,986 B2 | 6/2013 | Schraga | |
| 8,709,032 B2 | 4/2014 | Schraga | |
| 8,971,982 B2 | 3/2015 | Schraga | |
| 9,282,918 B2 | 3/2016 | Schraga | |
| 9,289,161 B2 | 3/2016 | Schraga | |
| 10,456,069 B2 | 10/2019 | Trissel | |
| 2003/0212344 A1 | 11/2003 | Yuzhakov | |
| 2004/0039302 A1 | 2/2004 | Kim | |
| 2004/0162573 A1 | 8/2004 | Kheiri | |
| 2005/0125017 A1 | 6/2005 | Kudrna | |
| 2005/0125019 A1 | 6/2005 | Kudrna | |
| 2005/0159768 A1 | 7/2005 | Boehm et al. | |
| 2005/0234492 A1 | 10/2005 | Tsai et al. | |
| 2005/0234495 A1 | 10/2005 | Schraga | |
| 2005/0283177 A1 | 12/2005 | Chen | |
| 2006/0100655 A1 | 5/2006 | Leong et al. | |
| 2006/0100656 A1 | 5/2006 | Olson et al. | |
| 2006/0224172 A1 | 10/2006 | LeVaughn et al. | |
| 2006/0247671 A1 | 11/2006 | LeVaughn | |
| 2006/0264996 A1 | 11/2006 | LeVaughn et al. | |
| 2007/0055298 A1 | 3/2007 | Uehata et al. | |
| 2007/0083222 A1 | 4/2007 | Schraga | |
| 2007/0100364 A1 | 5/2007 | Sansom | |
| 2007/0173874 A1 | 7/2007 | Uschold et al. | |
| 2007/0173875 A1 | 7/2007 | Uschold | |
| 2008/0027474 A1 * | 1/2008 | Curry | A61B 5/150519 606/181 |
| 2008/0082117 A1 | 4/2008 | Ruf | |
| 2008/0146966 A1 | 6/2008 | LeVaughn et al. | |
| 2008/0147108 A1 | 6/2008 | Kennedy | |
| 2008/0195133 A1 * | 8/2008 | Zhong | A61B 5/150022 606/181 |
| 2008/0255598 A1 | 10/2008 | LeVaughn et al. | |
| 2009/0030441 A1 | 1/2009 | Kudrna et al. | |

* cited by examiner

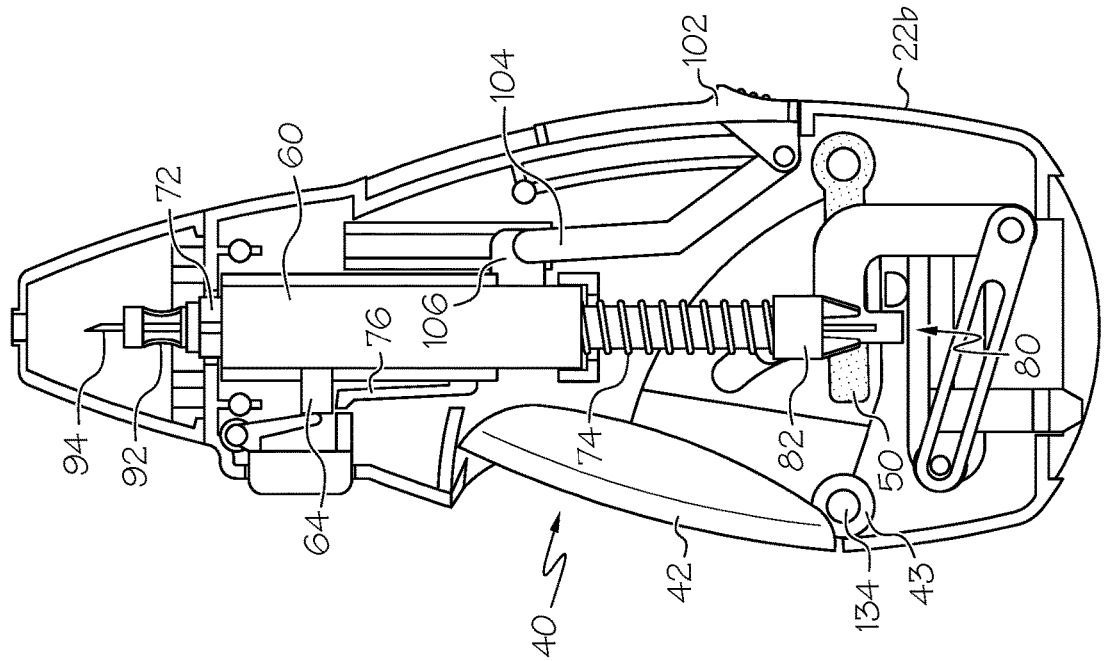
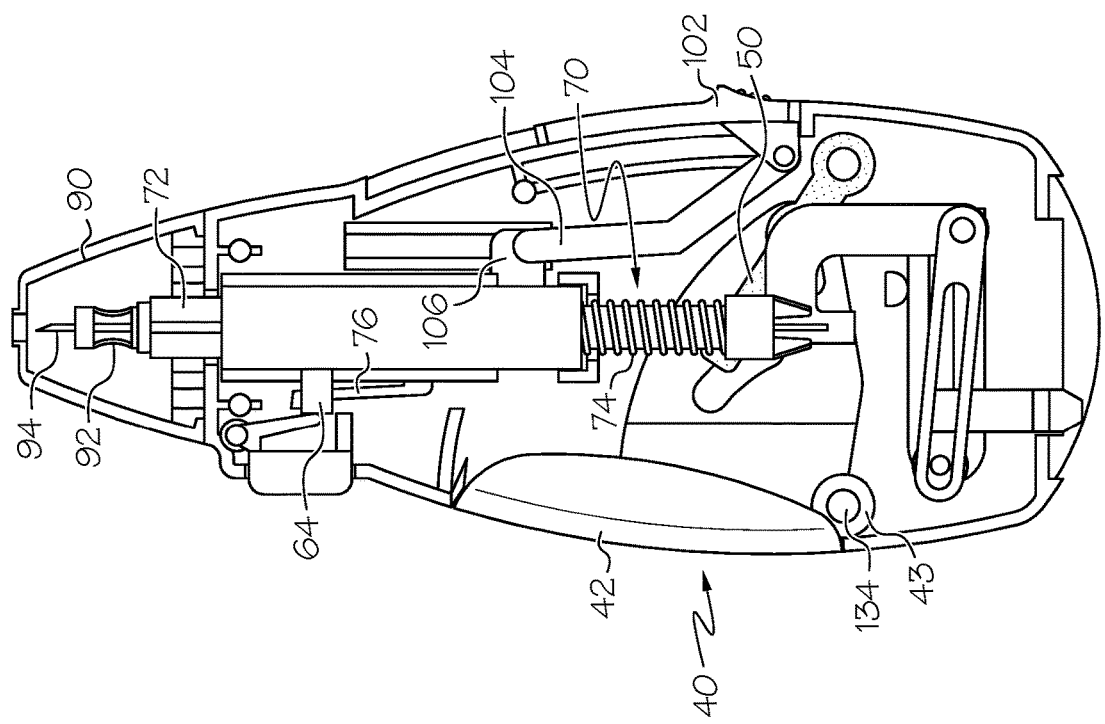

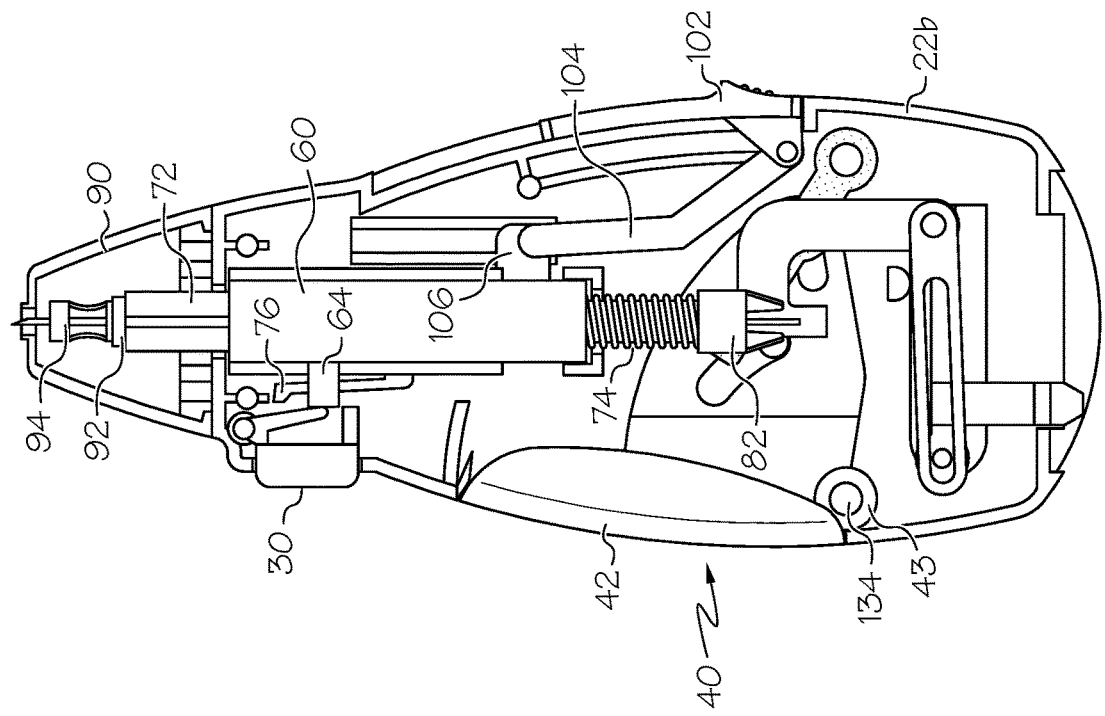
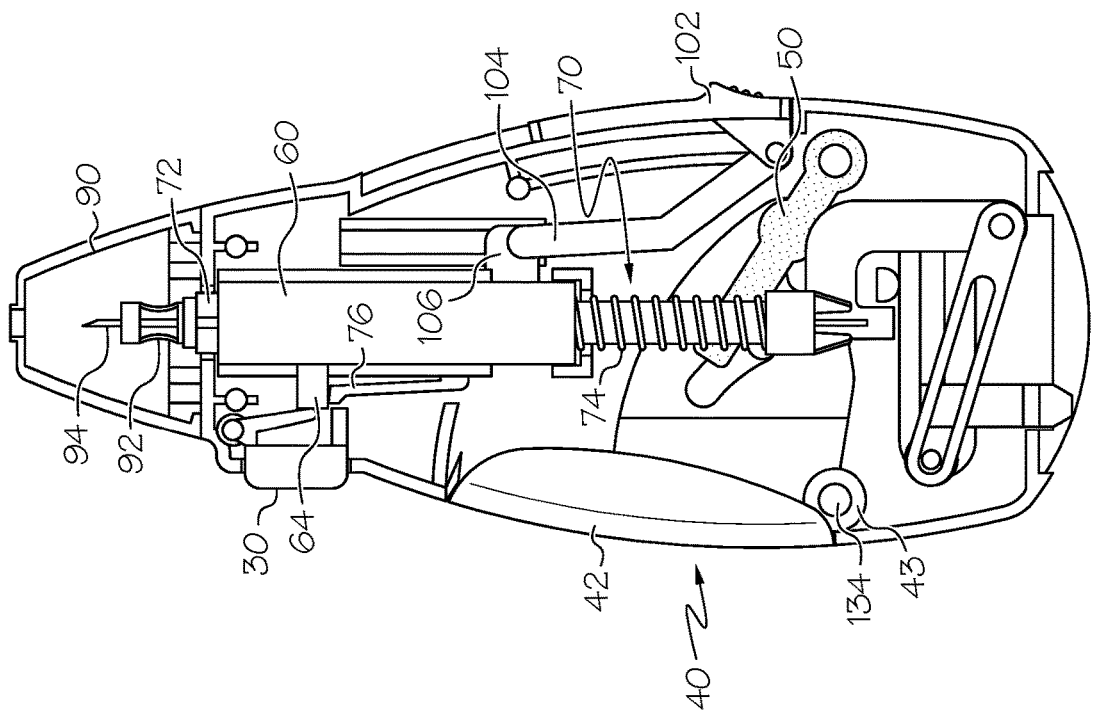
FIG. 7C
FIG. 7D

LANCING DEVICE WITH SIDE ACTIVATED CHARGE AND EJECT MECHANISMS

CROSS-REFERENCE TO RELATED APPLICATION

This application is a continuation of U.S. Non-Provisional patent application Ser. No. 13/860,270 filed Apr. 10, 2013, which claims the priority benefit of U.S. Provisional Patent Application Ser. No. 61/623,276 filed Apr. 12, 2012, the entireties of which are hereby incorporated herein by reference for all purposes.

TECHNICAL FIELD

The present invention relates generally to the field of medical devices, and more particularly to a lancing device for blood sampling and testing, and incorporated mechanisms for charging and/or ejecting the lancet by pivoting or transversely articulating a portion of the mechanism into the lancing device.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation.

A lancet is typically propelled by the drive mechanism from a retracted position within the housing to an extended position wherein a sharp tip portion of the lancet projects from the housing to prick the subject's skin at a desired lancing site. Optionally, an ejection mechanism may be incorporated into the lancing device for removal of the lancet after use. Many known lancing devices commonly use charging and/or lancet ejection mechanisms that function by pulling and/or pushing the mechanism generally away from the body of the lancing device, resulting in the user having to perform the charging and/or lancet ejection procedure by actuating or pulling a portion of the respective mechanism away from the body of the lancing device. Actuating the charging and/or ejection mechanism by pulling a portion of the mechanism away from the body of the lancing device can present challenges to users with reduced manual dexterity, and may require the subject or user to use two hands to hold the device body and pull the handle until the device is charged or the lancet is ejected.

Continuing improvement to charging and/or ejecting of lancing devices is sought. It is to the provision of improved lancing devices and methods of operation and use thereof that the present invention is primarily directed.

SUMMARY

In example embodiments, the present invention provides a lancing device having an improved charging and/or ejection mechanism. Additional example embodiments of the present invention provide improved methods of use of lancing devices.

In one aspect, the present invention relates to a lancing device with a housing with a longitudinal axis extending between a proximal end and a distal end. The lancing device includes a lancet carrier translationally mounted for axial movement within the housing. The lancing device also includes a drive mechanism secured to the lancet carrier to drive the lancet carrier through a lancing stroke. The lancing device further includes a charging mechanism with an actuator pivotally mounted to the housing. The charging mechanism is engaged with respect to the drive mechanism to charge the drive mechanism during pivotal movement.

In another aspect, the invention relates to a charging mechanism for a lancing device with a housing and a drive mechanism for driving a lancet carrier through a lancing stroke. The charging mechanism includes a pivotally mounted actuator with an input portion extending into the housing and an elongate portion rotatably mounted with respect to the input portion. The elongate portion is removably engaged with respect to the drive mechanism to apply a releasable charging force to the drive mechanism.

In still another aspect, the invention relates to a lancing device for carrying a lancet through a lancing stroke. The lancing device includes a housing with a longitudinal axis extending between a proximal end and a distal end and a lancet carrier translationally mounted for axial movement within the housing. The lancing device also includes an ejection mechanism with an actuator mounted to the housing, an elongate portion extending within the housing, and a linkage driven by the elongate portion toward the housing distal end. The linkage is engaged with respect to the lancet carried in the lancet carrier.

In yet another aspect, the invention relates to an ejection mechanism for a lancing device with a housing and a drive mechanism for driving a lancet carrier through a lancing stroke. The ejection mechanism includes an actuator mounted with respect to the housing and includes an elongate portion with a free en extending into the housing and an ejector finger engaged with respect to the lancing device.

In still another aspect, the invention relates to a method of charging a lancing device. The method includes pivotally mounting a charging mechanism within a portion of the lancing device. The method also includes pivotally mounting a linkage within a portion of the lancet carrier. The method also includes movably mounting a portion of the linkage to the charging mechanism. The method further includes pressing the charging mechanism into the lancing device to drive the arm and engage a lancet carrier. The method also includes retracting the lancet carrier to charged the lancing device.

In yet another aspect, the invention relates to a method of ejecting a lancet from a lancing device. The method includes pivotally mounting an ejection mechanism within a portion of the lancing device and pivotally mounting a linkage to a portion of the ejection mechanism. The method includes movably mounting a linkage within a lancet carrier and pressing the ejection mechanism into the lancing device. The method includes traversing the linkage within the lancet carrier to engage a lancet and removing the lancet from the lancing device.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 7A-7D are top views of the lancing device of FIG. 1 with portions of its external housing removed, showing the sequential operation moving between a neutral state, a charging state, a charged state, and a fully extended state.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
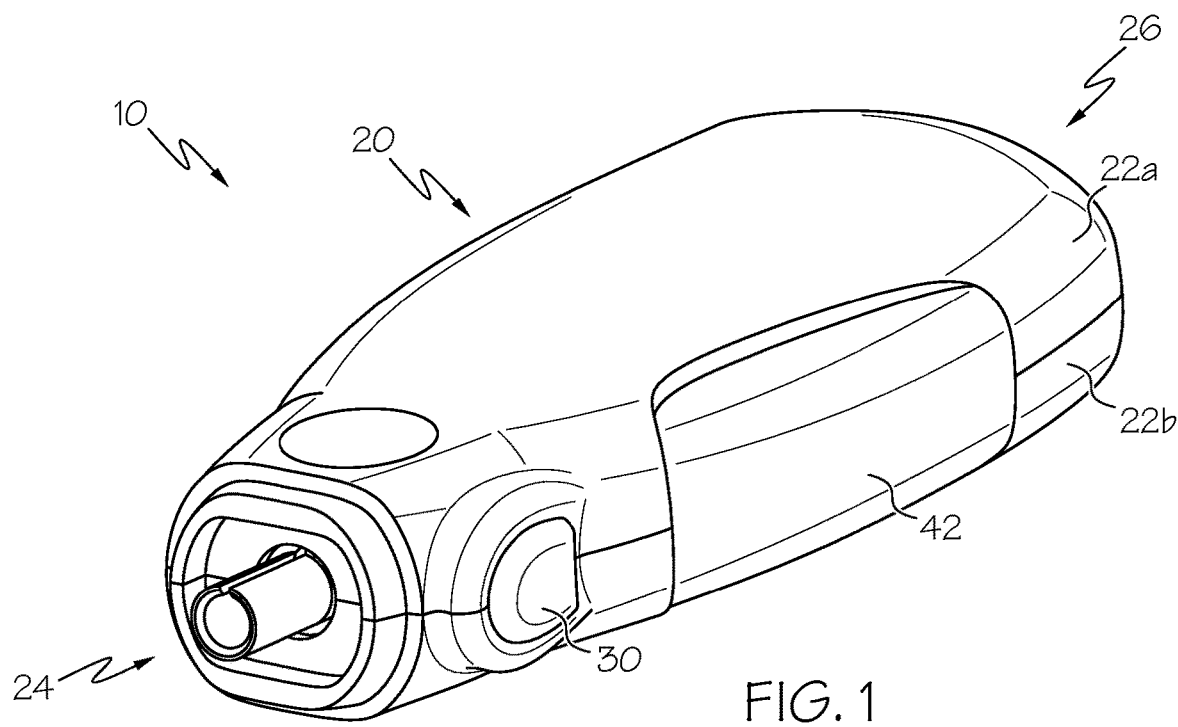
FIG. 1 is a front perspective view of a lancing device according to an example embodiment of the present invention.
Figure 2:
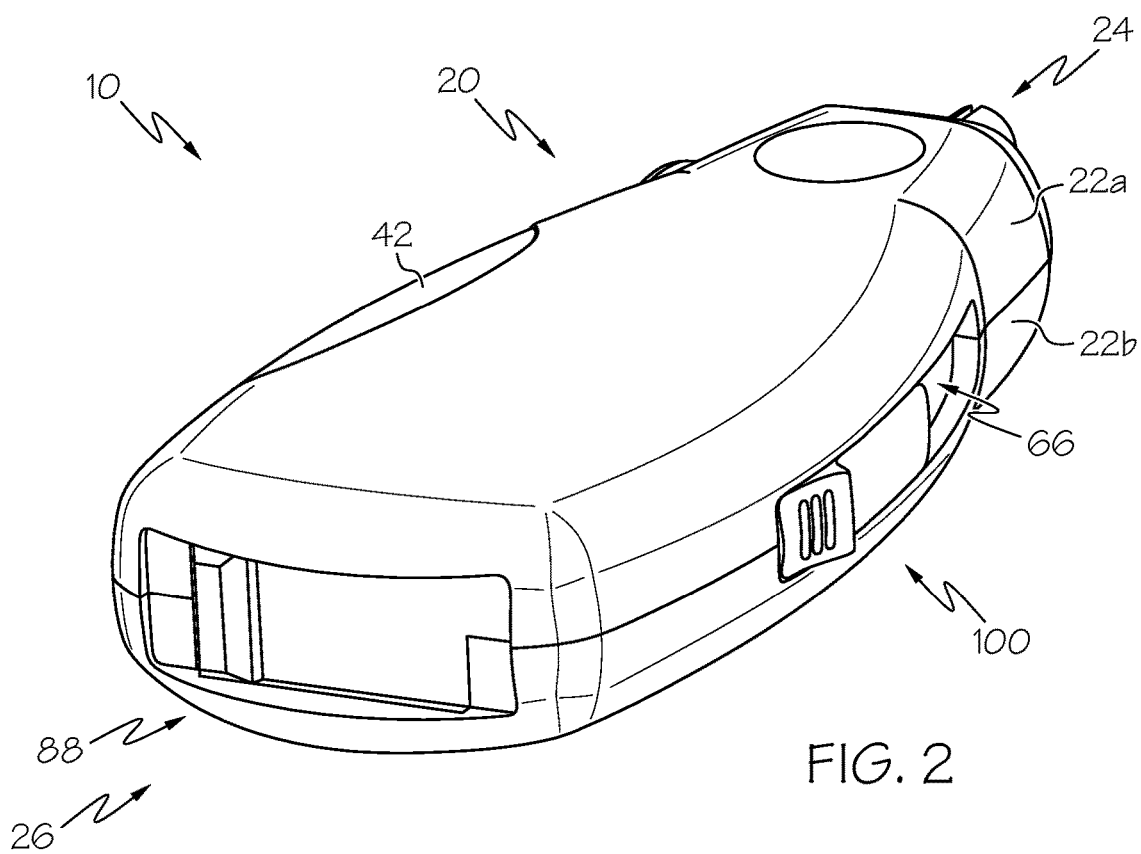
FIG. 2 is a rear perspective view of the lancing device of FIG. 1.

With reference now to the drawing figures, wherein like reference numbers represent corresponding parts throughout the several views, FIGS. 1-13 show various aspects and features of a lancing device 10 according to example forms of the invention. As best shown in FIGS. 1-2, the lancing device 10 includes a housing 20 generally comprising separable upper 22a and lower 22b housing shells, and a forward or distal end 24 defining a lancet opening through which at least a sharp tip portion of a lancet projects at the extended position of the lancing stroke to penetrate the skin of a subject during the lancing process. The housing 20 protects a lancet carrier 70 that is movably housed within the shells 22a, 22b. As depicted, the housing 20 has a generally elongate ergonomic shape, wider at the back and tapering to a narrower front; however, alternate housing shapes can be utilized. The housing 20 preferably has a lengthwise dimension, in an axial direction between the forward end 24 and rear or proximal end 26, that is greater than its side-to-side width in a transverse dimension, which in turn is greater than its thickness from top-to-bottom. The housing 20 can be constructed of a substantially rigid durable material, for example plastic or composites, in example embodiments.

A release button 30 projects through a side opening formed in the shells 22a, 22b to release a trigger mechanism when depressed, as shown in FIG. 7C. The release button 30 actuates the device to propel the lancet carrier 70 along a lancing stroke from a charged or retracted position within the housing 20, as best shown in FIGS. 7B, to an extended or lancing position, as best shown in FIG. 7D. In the extended position, at least the sharp tip portion of the lancet projects outwardly of the lancet opening at the distal end 24 of the housing 20.

FIGS. 1-7 show a charging mechanism 40 that has a charging actuator or user-actuated arm 42 positioned within a portion of one side contour of the housing shells 22a, 22b. When actuated, the charging mechanism 40 retracts the lancet carrier 70 and energizes a biasing spring 74 to provide motive force to propel the lancet carrier along the lancing stroke when the device is actuated by depressing the release button30. In example embodiments, the charging actuator 42 pivotally mounts to the housing 20 at one end, and aligns with and fills a void or cut-out portion on one side of the housing shells 22a, 22b to generally form a generally continuous and smoothly radiused side portion of the outer contour of the lancing device 10. When the charging actuator 42 is pressed or squeezed transversely inwardly toward the central longitudinal axis of the housing 20, the charging actuator pivots or translates into the housing, operating through a linkage providing mechanical advantage to retract the lancet carrier 70 and charge the drive mechanism of the lancing device. As depicted, the charging actuator 42 can be a separate body from the housing 20 or alternatively an integral flexing or otherwise articulated part of the housing (not shown). The transversely-operated charging mechanism 40, with the charging actuator 42, is operated by squeezing inwardly into the housing 20 to allow a user to charge the lancing device's drive mechanism with one hand in an intuitive and ergonomic manner, and provide a degree of mechanical advantage for ease of operation.

Optionally, the lancing device 10 can include a depth-adjust mechanism 88, an endcap or nose-cone portion 90, and/or an ejection mechanism 100. As depicted, a proximal end 26 of the lancing device 10 includes a portion of the depth-adjust mechanism 88 including an elongated opening or slot through which a distal positioning tab or slider extends, movable within the limits of the opening, to increase or decrease the depth or extension of the lancet tip projecting external of the housing. As best shown in FIGS. 12A-13B, removal of the endcap 90 allows access for removal and replacement of the lancet after use, for example by actuation of the ejector handle 102. The ejector handle 102 movably mounts within an elongated opening 103 along a side of the housing 20 generally opposite the charging actuator 42 and extends within the housing to selectively engage and eject the lancet.

Figure 3:
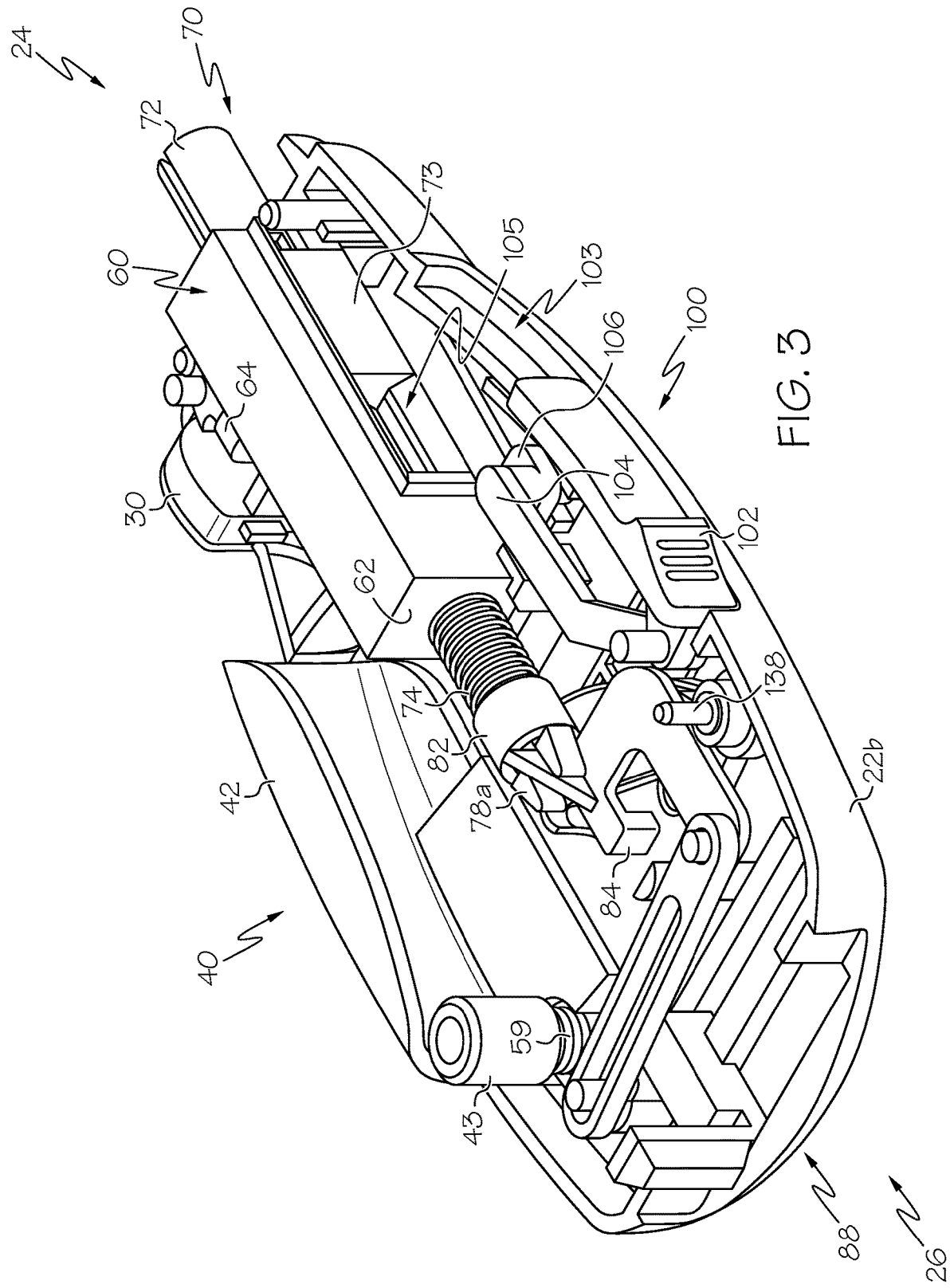
FIG. 3 shows the lancing device of FIG. 1 with portions of its external housing removed to show internal components thereof.

FIG. 3 shows the lancing device with its upper housing shell 22a removed. An inner drive core 60 is engaged in a fixed position within the housing 20 by one or more interengaging pin and receiver connections or other interengaging surface features, as is shown in greater detail in FIG. 6. In example embodiments, a portion of an inner drive mechanism is translationally mounted to slide within an axial bore or channel 66 through the inner drive core 60. As depicted, the drive mechanism includes the lancet carrier 70 that has a collar or sleeve 72 at a distal end thereof for releasably engaging a lancet. The biasing spring or combination drive-and-return spring 74 is engaged between a proximal wall 62 of the drive core 60 and a coupling or spring retainer 80. The spring 74 propels the lancet carrier 70 along the forward portion of the lancing stroke, and subsequently returning the lancet carrier to a retracted position within after the lancing has been completed. Optionally, separate drive and return springs can be used as desired. For example, an additional biasing spring can be included between arms 73 on the carrier 70 and the interior portion of the proximal wall 62 to function as a drive spring in order to propel the lancet carrier along the forward portion of the lancing stroke. The biasing spring 74, can function as a return spring to return the lancet carrier 70 to a retracted position within the housing 20.

A cantilevered release finger 76 projects from the axial shaft of the lancet carrier 70 for releasable engagement with a catch surface 64 of the drive core 60, as best shown in FIG. 7C, to retain the lancet carrier in its retracted position when the device is charged. The release finger 76 is contacted, and depressed/deflected, by the release button 30 being pressed to release the lancet carrier 70 to travel along its lancing stroke and thereby initiate the lancing procedure. As depicted, the proximal end of the lancet carrier 70 includes a split yoke having a pair of resilient forks or barbs 78a, 78b to permit installation and retention of the biasing spring 74. As depicted, an axially oriented bore or collar 82 of the spring retainer 80 is secured at the proximal end of the lancet carrier 70 with the resilient forks 78a, 78b, for example with interengaging surface features.

The depth-adjust mechanism 88 generally includes a pivotal link having one end pivotally mounted to a portion of the spring retainer 80 and having another end pivotally mounted to the distal positioning tab. One or more releasable index detents are optionally provided between the positioning tab and the housing to secure the positioning tab in a user-selected position in the elongated opening on the housing, to permit indexed movement; or alternatively a continuously variable positional adjustment is provided. When the lancet carrier 70 is released to travel along its lancing stroke, the pivotal link abuts an engagement post within the lower housing shell 22b, functioning as a fulcrum about which the link pivots, to restrict the penetration or lancing depth of the lancing stroke. As depicted, the depth adjust mechanism 88 is positioned for minimum penetration by maximizing the length between the distal positioning tab and the engagement post. Alternatively, the positioning tab can be positioned at one or more intermediate points between the minimum and maximum penetration settings. Further description of the example depth-adjustment mechanism 88 is presented in the Applicant's U.S. Provisional Patent Application No. 61/622,570 filed Apr. 11, 2012, which is hereby incorporated by reference for all purposes.

The ejection mechanism 100 generally includes an actuator or user-actuated portion 102 that is movably mounted within an elongated slot 103 on the side of the lancing device. As depicted, a portion of a handle 102 extends internally within the housing 20 and pivotally mounts to a link 104. As shown, the link 104 can have an angled elbow shape with a distal end and a proximal end, which pivotally mounts to the handle 102. The distal end of the link 104 extends within the housing 20 and pivotally mounts to a finger 106 that is slidably or translationally mounted within a portion of the lancet carrier 70. Generally, the lancet carrier 70 includes an elongated slot or channel 66 for accommodating the finger 106 during the lancing procedure. When a used lancet is to be ejected, the endcap 90 is removed and the actuator handle 102 is pushed or pressed in an distal or forward direction, which forces the finger 106 in a distal or advancing direction within the channel 66 to selectively engage and eject the used lancet outwardly from the sleeve 72.

Figure 6:
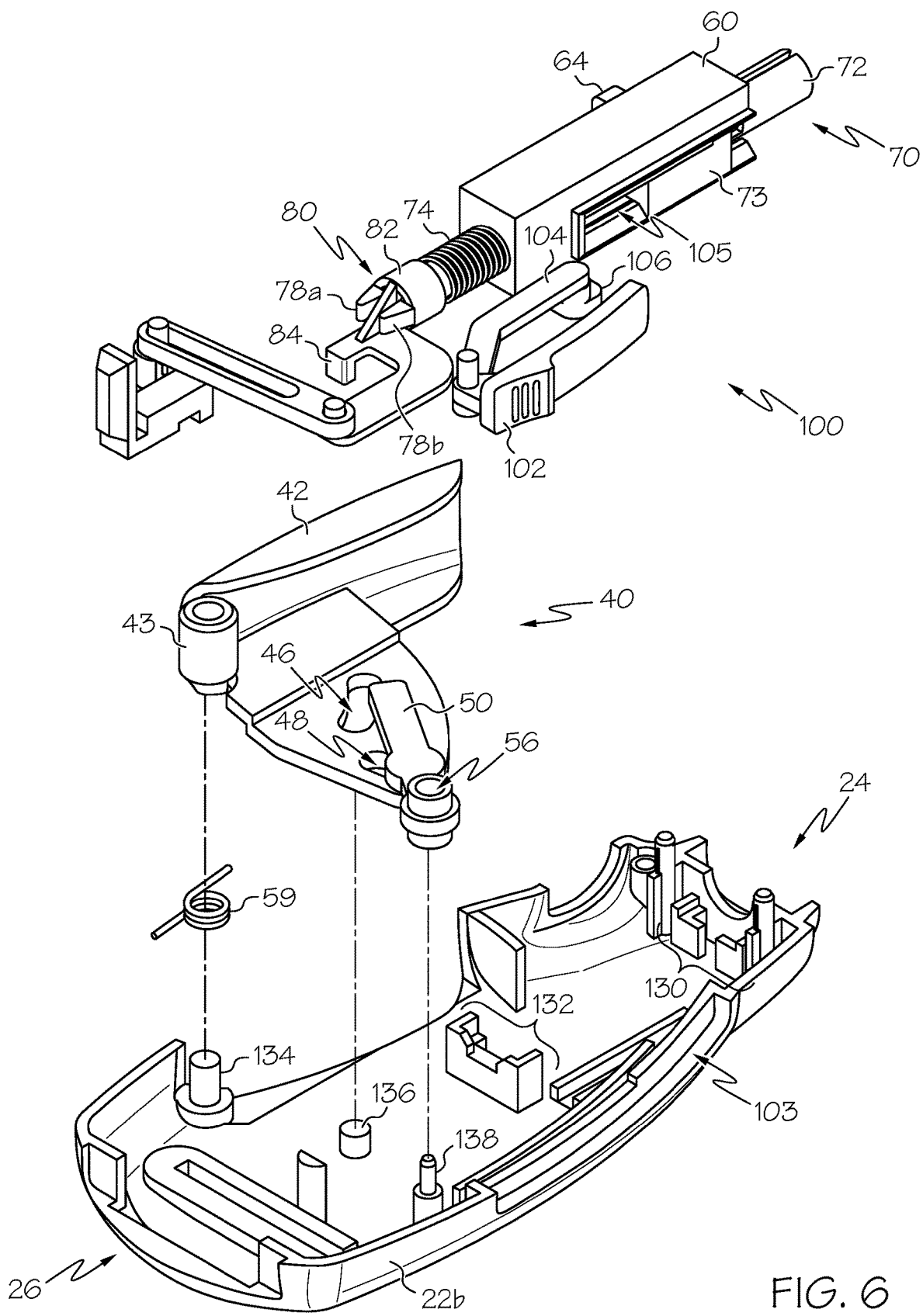
FIG. 6 is a partial assembly view of the lancing device of FIG. 1 with portions removed to show internal components thereof.

The pivoting cam linkage or charging mechanism 40 generally includes the charging actuator 42 and an arm 50, each pivotally mounted to portions of the lower housing shell 22b, as best shown in FIGS. 6-7. Pivoting the actuator 42 within the housing 20 proximally drives the arm 50 to engage a tab or surface feature 84 on the spring retainer 80. When engaged, the arm 50 drives the tab 84 toward the housing proximal end 26, which correspondingly retracts the lancet carrier 70 to the charged state. Preferably, the charging mechanism 40 provides a degree of mechanical advantage to operation of the arm 50 that contacts the tab or surface feature 84 when retracting the lancet carrier 70 to the charged state.

Figure 4:
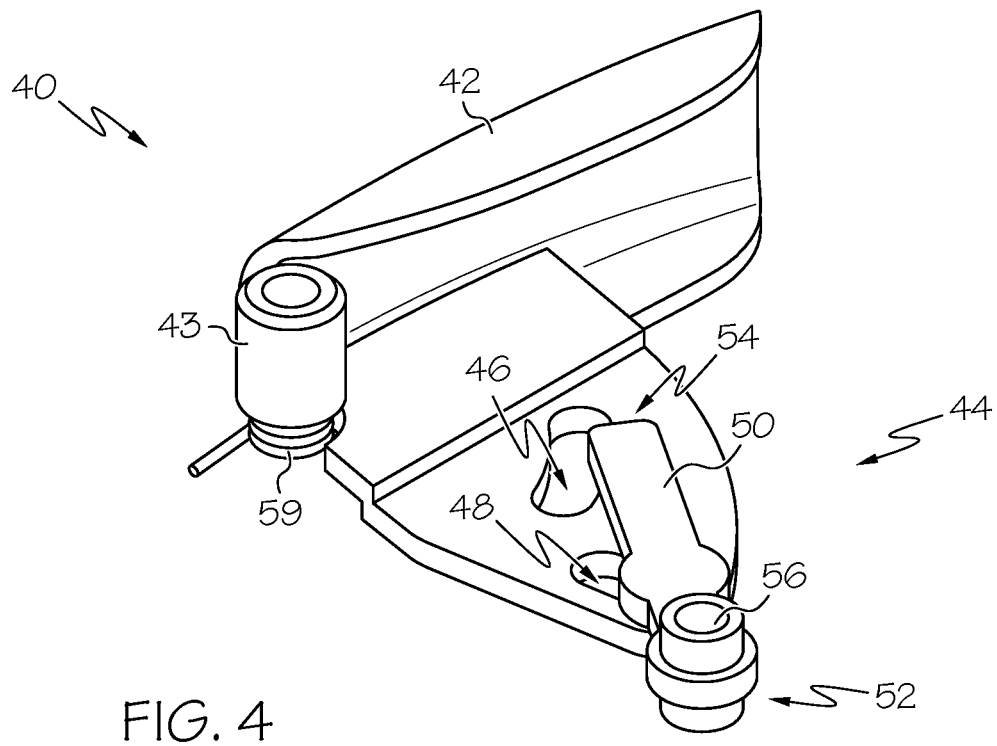
FIG. 4 is a top perspective view of the charging mechanism of the lancing device of FIG. 1.
Figure 5:
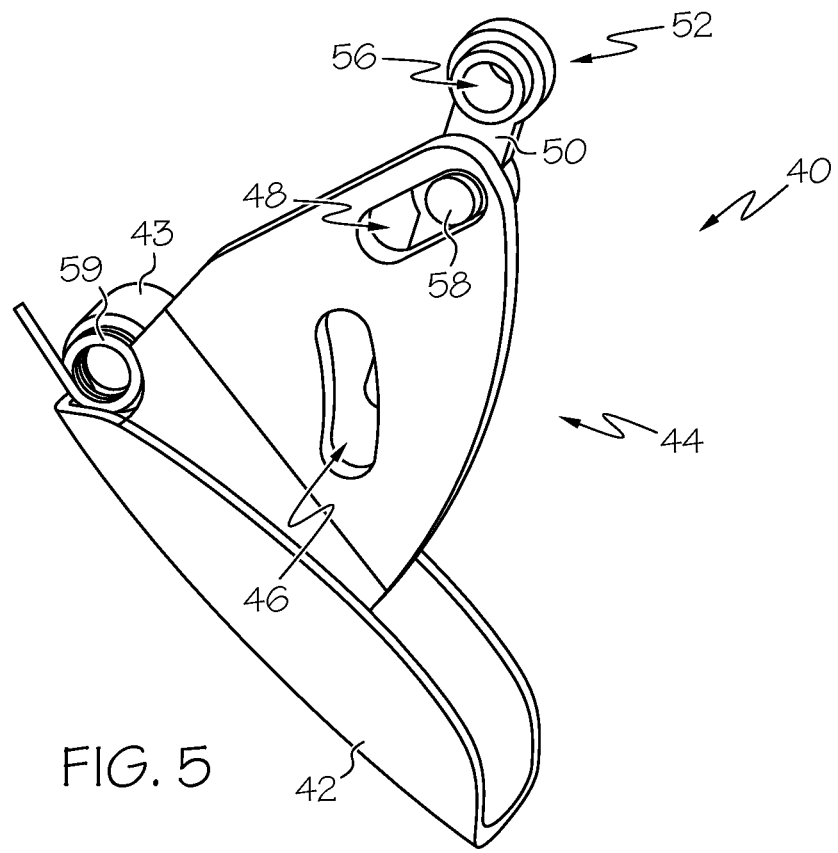
FIG. 5 is a bottom perspective view of the charging mechanism of the lancing device of FIG. 1.

FIGS. 4-5 show details of the charging mechanism 40. In the depicted embodiment, the charging handle or actuator 42 generally has an arcuate or radial U-shaped or C-shaped cross-sectional profile to fill the void of the housing 20 and align with the contour of the housing. The charging actuator 42 includes a pivot sleeve or collar 43 to pivotally mount to an axle or pin portion 134 of the housing for actuation or pivoting thereon. Preferably, the charging handle 42 is sized and shaped to accommodate actuation by one hand or by one or more fingers of the user. A flange or internal portion 44 of the charging handle 42 includes one or more features for guiding and/or driving portions of the charging mechanism 40. For example, a slot 46 for guidance, alignment and support slidably receives a guide post 136 extending upwardly from the lower housing shell 22b. The flange 44 also has a slot 48 for receiving a guiding portion 58 of the pivotal arm 50 therein to be driven upon actuation of the charging handle 42.

The arm 50 generally includes an elongated member having a pivot end 52 and a free end 54 generally opposite thereto. The pivot end 52 includes a pivot sleeve 56 to pivotally mount to a pin or post 138 extending from the lower housing shell 22b. The free end 54, or a portion proximal thereto, is provided for selectively engaging the surface feature tab 84 of the spring retainer 80. The guiding portion 58, for example a pin or probe, generally extends between the midpoint of the arm 50 and the pivot end 52, and is provided for movably mounting within the slot 48.

FIG. 6 shows a partial assembly view of the lancing device 10, including the charging mechanism 40 and the lower housing shell 22b. As depicted, interengaging surface features 130, 132 near the distal end 24 are provided to engage the proximal and distal ends of the inner drive core 60 in a fixed position within the lower housing shell 22b. A proximal portion of the lower shell 22b includes the pivot post 134 for engaging the pivot sleeve 43 of the charging handle 42, the post 138 for engaging the pivot sleeve 56 of the arm 50, and the guiding pin or feature 136 movably inserting within the slot 46 in order to guide and support the flange 44. Optionally, a biasing spring 59 can be provided between the pivot sleeve 43 and the pivot post 134 for biasing the charging handle 42 towards a closed or unactuated position wherein the handle 42 aligns with the contour of the housing 20.

FIGS. 7A-D show the sequence of operation of the lancing device 10 throughout the charging and actuation portions of the lancing procedure. As depicted, the charging actuator 42 pivots (clockwise in the depicted view) from an unactuated neutral position (FIG. 7A) wherein the pivotally mounted elongate arm 50 is generally angularly offset from the elongated axis of the lancet carrier 70, to an actuated position (FIG. 7B), driving the arm 50 to pivot (counter-clockwise in the depicted view) and position transverse to the elongated axis of the lancet carrier 70. As the arm 50 is driven to pivot (counter-clockwise in the depicted view) by the pivotal actuation (clockwise) of the charging actuator 42, the arm 50 engages the surface feature tab 84 of the spring retainer 80, further retracting the lancet carrier 70 to energize the biasing spring 74 and engage the release finger 76 with the catch surface 64 of the drive core 60 (FIG. 7C). After engaging the release finger 76 with the catch surface 64, the natural bias of the biasing spring 59 returns the charging handle 42 to an unactuated position and the arm 50 returns to being angularly offset relative to the elongated axis of the lancet carrier 70.

Upon actuating or depressing the release button 30 to disengage the release finger 76 from the catch surface 64, the charged biasing spring 74 propels the lancet carrier 70 along an advancing portion of the lancing stroke from the charged position within the housing 20 to an advanced position wherein at least the sharp lancet tip 94 projects externally of the housing 20 to penetrate the subject's skin at a lancing site (FIG. 7D). The biasing spring 74 subsequently returns the lancet carrier and the lancet to the neutral position (FIG. 7A). As described above, when the used lancet 92 is to be ejected, the endcap 90 is removed from the housing 20 and the ejector handle 102 is actuated forward, forcing finger 106 movably mounted within the lancet carrier 70 to engage and eject the lancet (shown in FIGS. 12A-13B).

In further example embodiments, as depicted in FIGS. 8-13, an alternative ejection mechanism 200 is pivotally mounted to the housing similarly to the charging mechanism described above. This ejection mechanism 200 ejects the lancet by actuating or pivoting an ejection actuator 202 into the housing 20 of the lancing device 10. The ejection mechanism 200 generally includes an ejection handle 202 having an elongate arm or interior portion 204, a link 211, and a finger 214. The ejection handle or user actuated portion 202 generally has a similar profile and contour as the charging actuator 42 described above, and is similarly sized and shaped to accommodate actuation or pivoting transversely inward into the housing 20, upon operation as by a user squeezing or pressing inwardly with one hand or with one or more fingers of the user.

Figure 8:
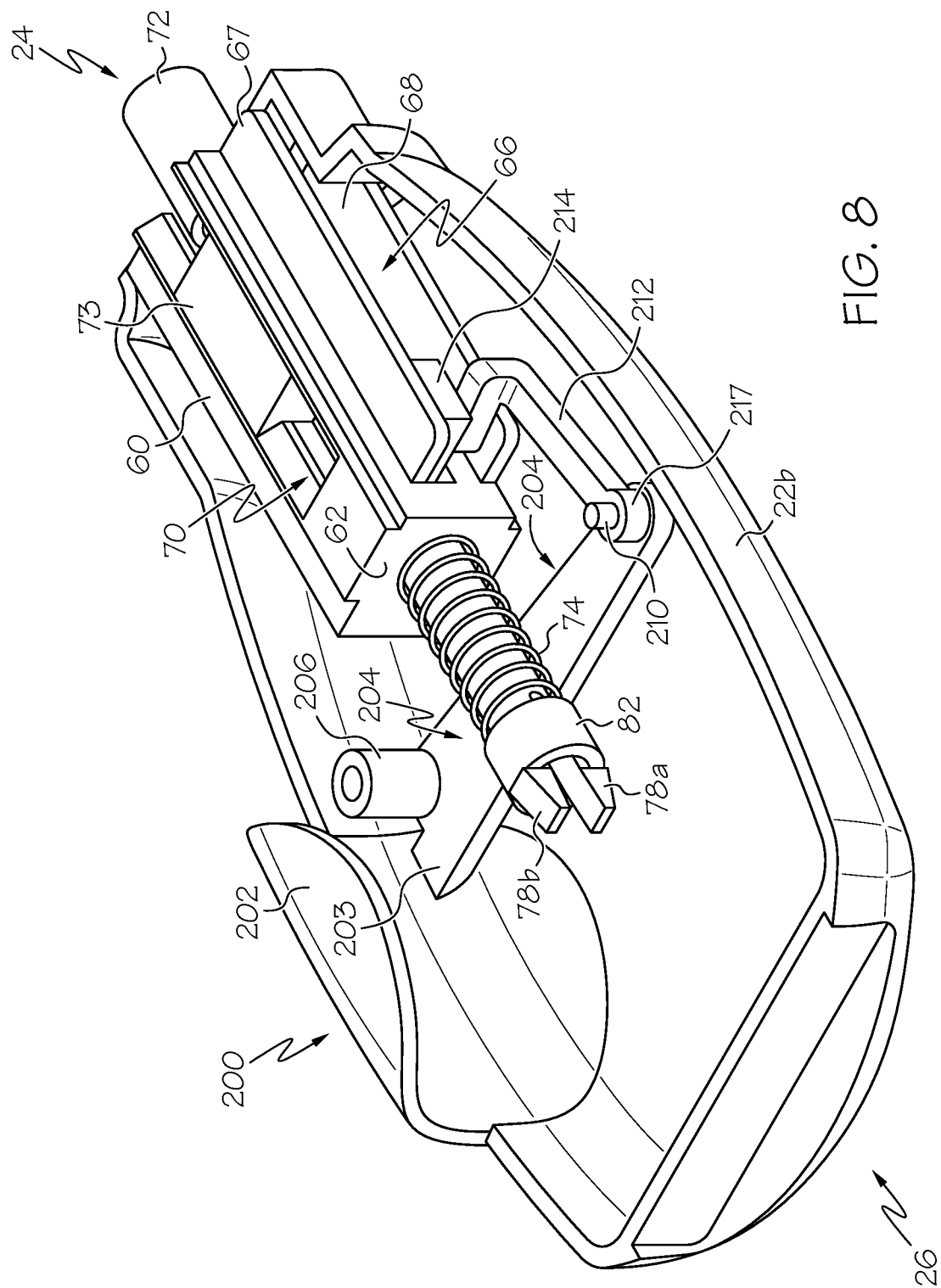
FIG. 8 is a perspective view of a lancing device with portions of its external housing removed to show internal components thereof, according to another example embodiment of the present invention.
Figure 9:
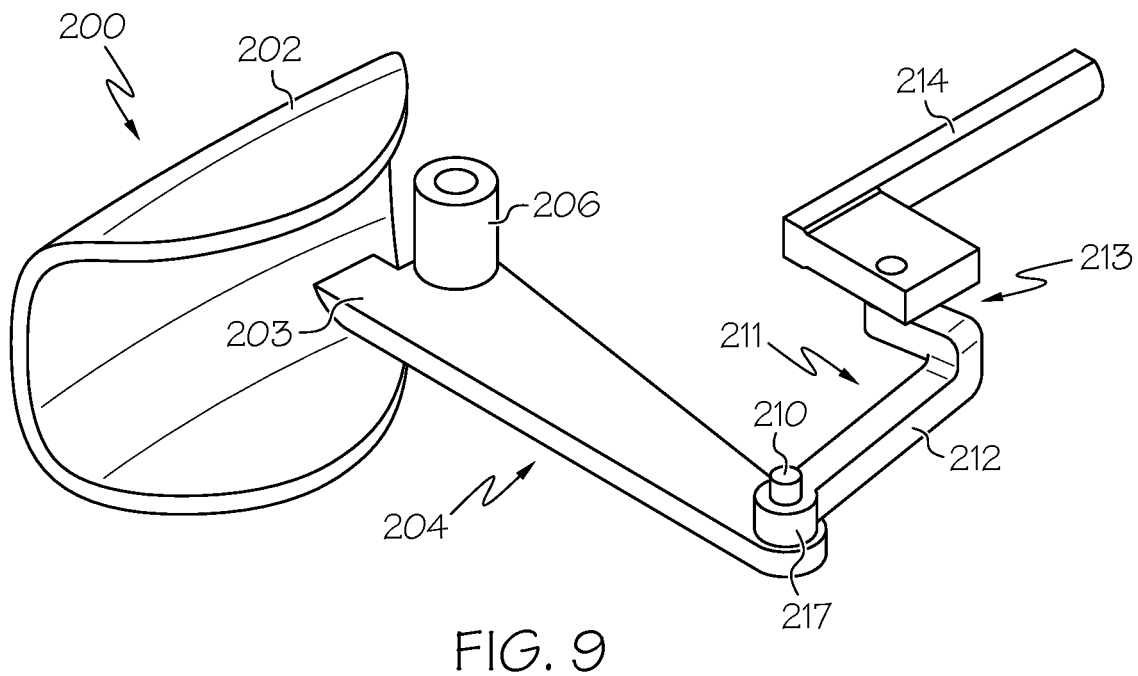
FIG. 9 is a top perspective view of the ejection mechanism of the lancing device of FIG. 8.
Figure 10:
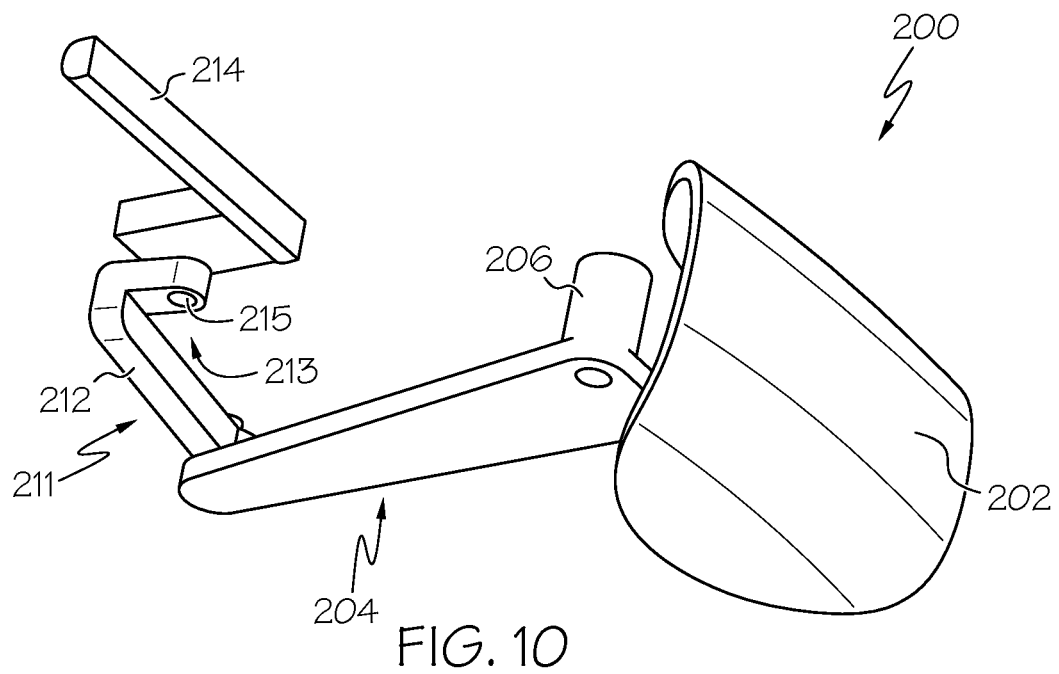
FIG. 10 is a bottom perspective view of the ejection mechanism of the lancing device of FIG. 8.

The elongate arm or interior portion 204, generally extending within the housing 20, includes a pivot sleeve 206 for pivotally mounting to a pivot post 234 of the lower housing shell 22b, and a pivot post 210 for pivotally mounting to the link 211 (shown in FIGS. 8-10). As depicted in FIGS. 9-10, the link 211 includes an L-shaped arm portion 212 having a pivot end pivotally mounted to the pivot post 210 of the interior portion 204, and a leg portion 213, generally transverse and axially offset from the arm 212 and pivotally mounted to a pivot post 215 of the finger 214.

Figure 11:
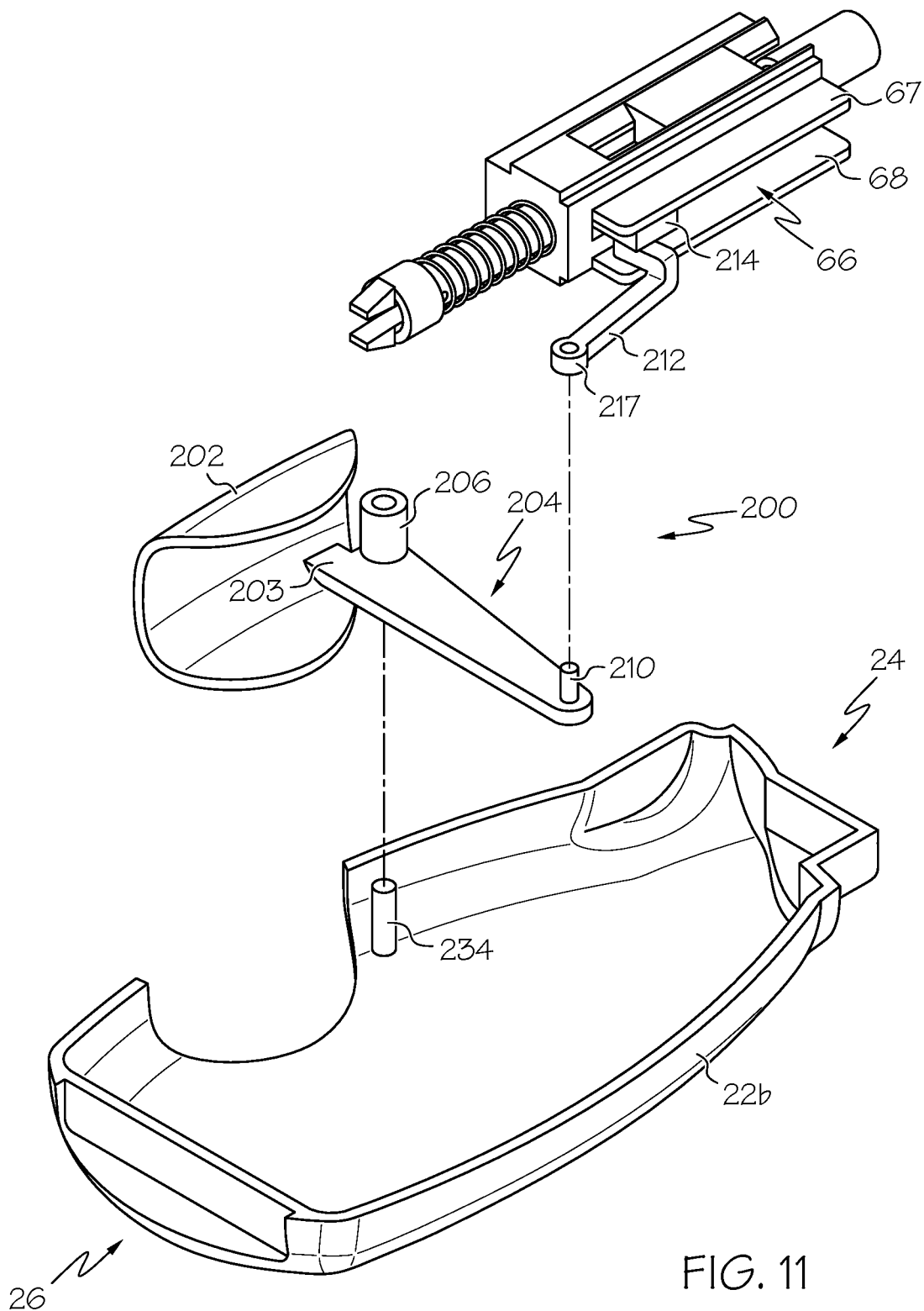
FIG. 11 is a partial assembly view of the lancing device of FIG. 8 with portions removed to show internal components thereof.
Figure 12B:
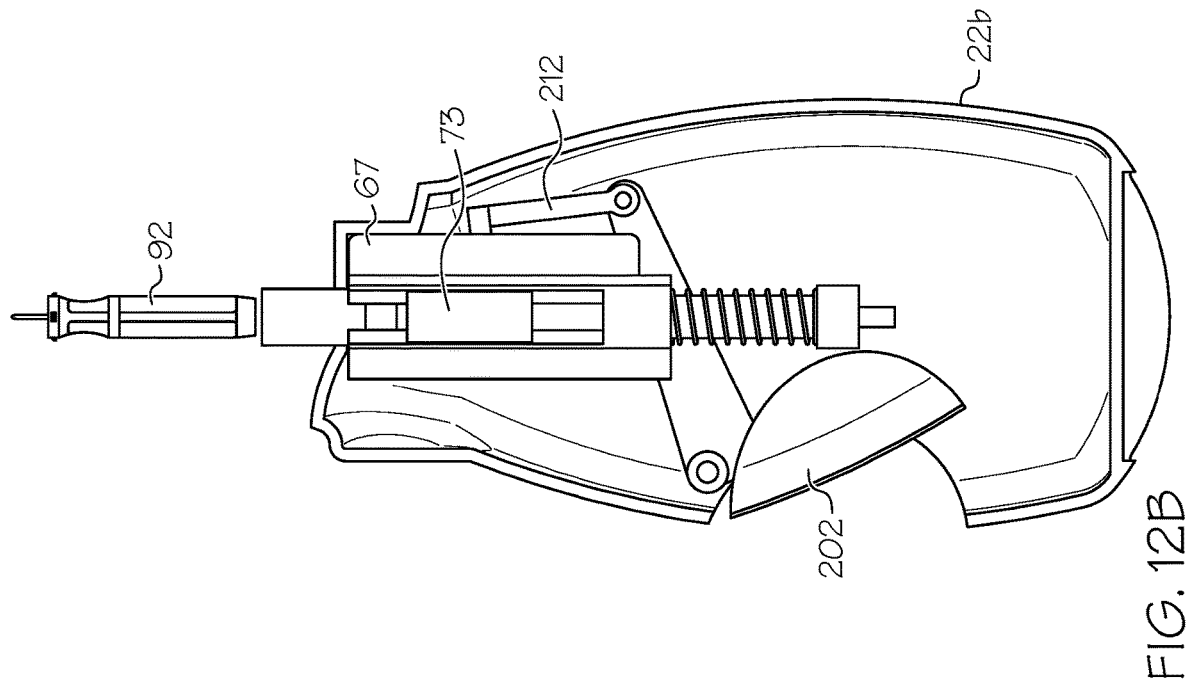
FIGS. 12A-B are top views of the lancing device of FIG. 8, showing the sequential operation of the lancet ejection mechanism moving from a neutral state to an ejection state.
Figure 12A:
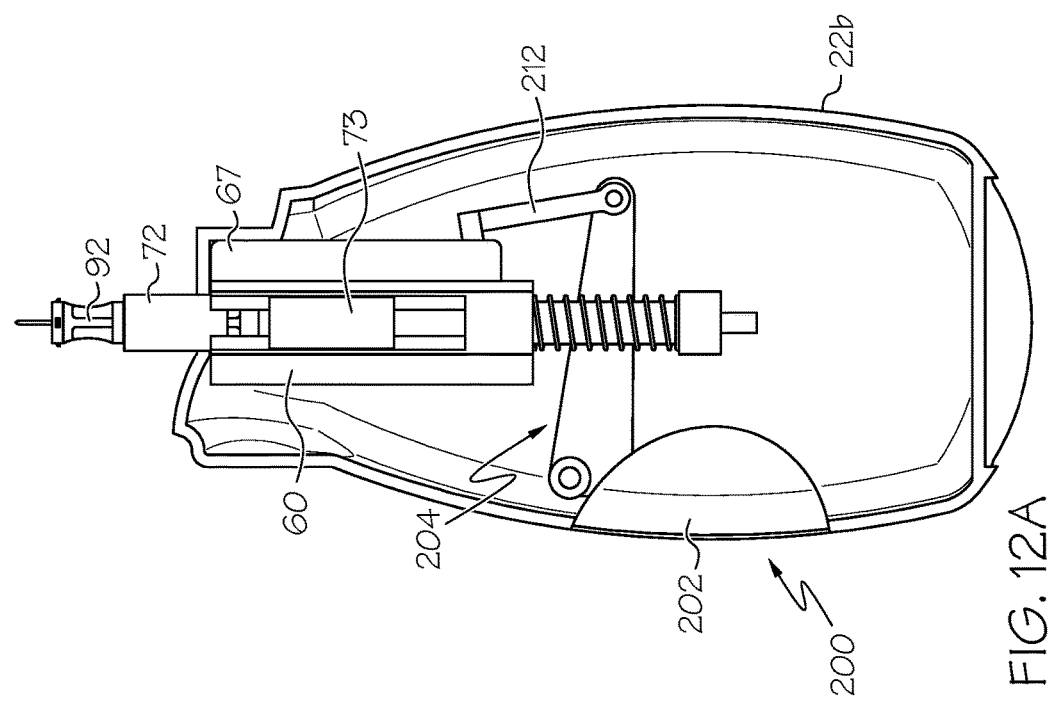
Figure 13B:
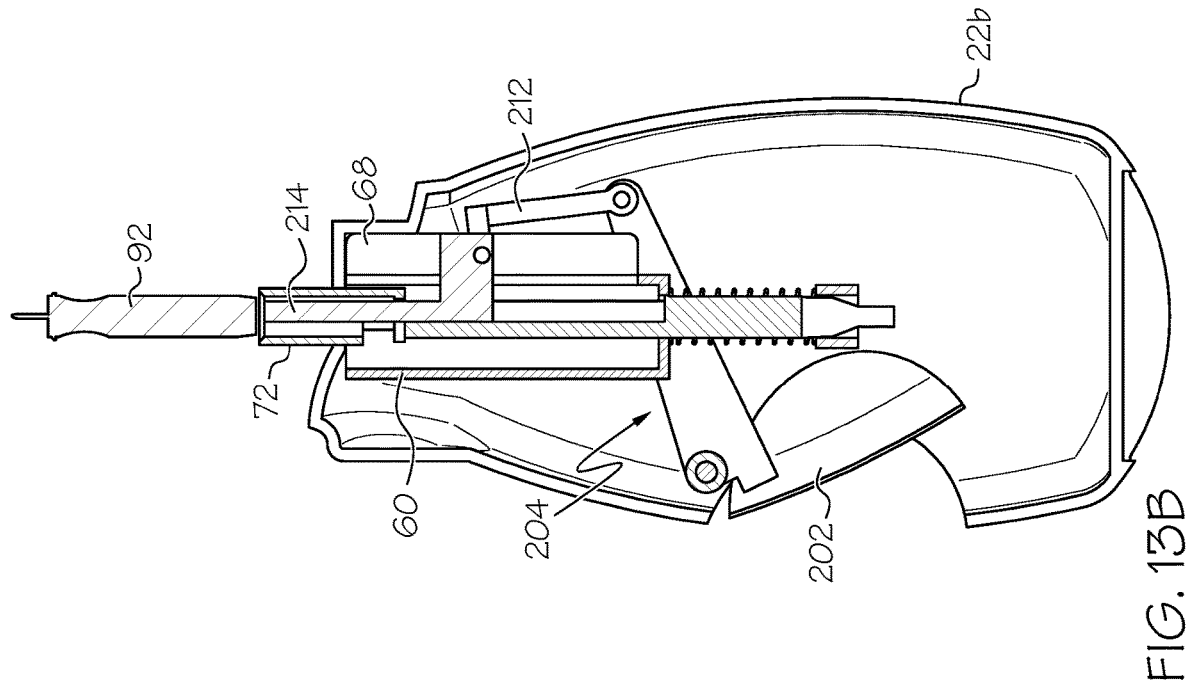
FIGS. 13A-B are cross-sectional views of the lancing device of FIGS. 12A-B, showing the sequential operation of the lancet ejection mechanism moving from a neutral state to an ejection state.
Figure 13A:
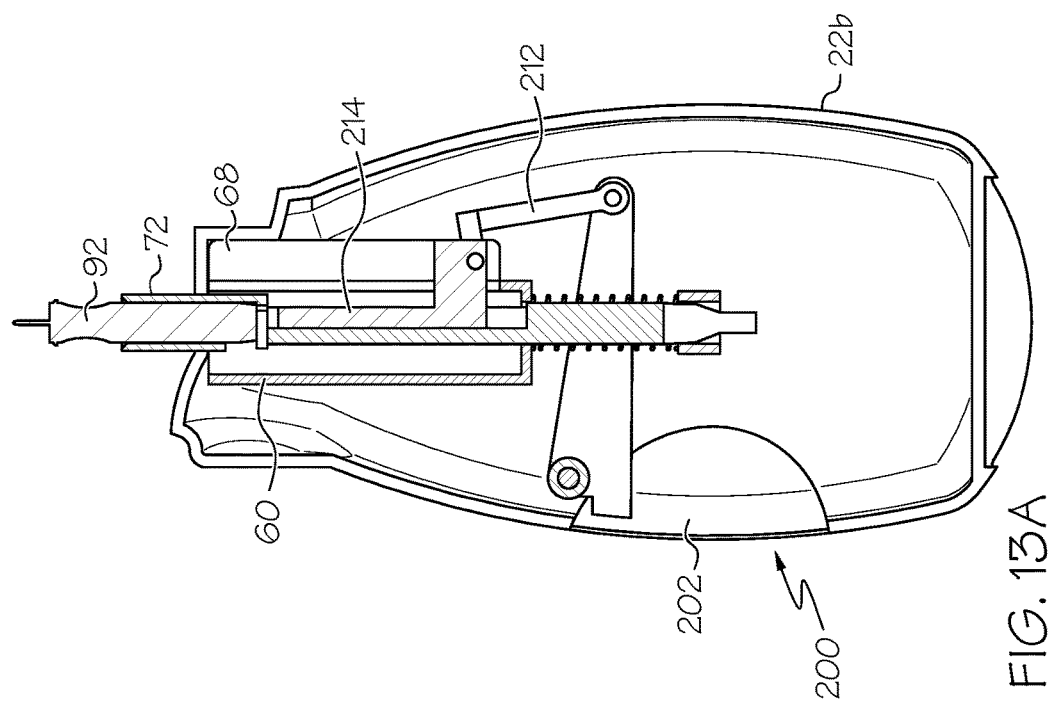

As shown in FIG. 11, the inner drive core 60 includes an elongate guide or channel 66 including walls 67, 68 for supporting and guiding the finger 214. The walls 67, 68 of the channel 66 align with the elongated slots of the inner drive core and the lancet carrier 70 such that the pivotally mounted leg portion 213 and finger 214 can freely traverse therein upon actuation of the ejection handle 202, subsequently advancing and retracting the finger within slots in the drive core and the lancet carrier to abut and remove or eject the lancet 92 from the sleeve 72 of the lancet carrier 70 (as shown in FIGS. 12A-B). FIGS. 13A-B show cross-sectional views of the lancing device 10 of FIGS. 12A-B to show additional features of components thereof, as described above.

The systems and methods of the example forms of the invention enable the user to charge the drive mechanism and/or eject the lancet by redirecting the pivotal motion of pushing or pressing the user actuated portions or actuators 42, 202 transversely inward toward the central longitudinal axis of the housing, through a cam or linkage mechanism, to result in an axial charging or ejection motion. The charging mechanism and/or ejection mechanism may include other mechanical linkages having pivotal links, slots, pins, cams, gears, pulleys, cords, cables, and/or any other mechanically advantaged linkages that can redirect motion or change the ratio between the length of the charging handle stroke and the length necessary to retract and charge the lancet carrier.

While the invention has been described with reference to preferred and example embodiments, it will be understood by those skilled in the art that a variety of modifications, additions and deletions are within the scope of the invention, as defined by the following claims.

What is claimed is:

1. An ejection mechanism for a lancing device comprising a housing and a drive mechanism for driving a lancet carrier through a lancing stroke, the ejection mechanism comprising:
   an actuator mounted with respect to the housing and comprising an elongate portion with a free end extending into the housing and
   an ejector finger pivotally connected to the elongate portion about a pivot axis such that the ejector finger and the elongate portion are configured to pivot relative to one another about the pivot axis, wherein the ejector finger is configured to be driven by the elongate portion to engage the lancet carried within the lancet carrier and eject the lancet from the lancet carrier.

2. The ejection mechanism of claim 1, wherein the actuator is pivotally mounted to the housing.

3. The ejection mechanism of claim 1, wherein the ejector finger is pivotally mounted with respect to the elongate portion free end.

4. The ejection mechanism of claim 1, further comprising a link pivotally connected to the elongate portion free end and connected to the ejector finger.

5. The ejection mechanism of claim 1, wherein the actuator is translationally mounted to the housing.

6. The ejection mechanism of claim 1, wherein the ejector finger is mounted with respect to the elongate portion free end.

7. The ejection mechanism of claim 1, further comprising a link connected to the elongate portion free end and connected to the ejector finger.

8. A method of ejecting a lancet from a lancing device, the method comprising:
- mounting an ejection mechanism within a portion of the lancing device,
- pivotally mounting a linkage to a portion of the ejection mechanism about a pivot axis such that the linkage and the ejection mechanism pivot relative to one another about the pivot axis,
- movably mounting the linkage within a lancet carrier,
- engaging the ejection mechanism,
- traversing the linkage within the lancet carrier to engage the lancet, and
- removing the lancet from the lancing device.

9. The method of ejecting a lancet from a lancing device of claim 8, wherein the method further comprises pivotally mounting the ejection mechanism within the lancing device and the ejection mechanism is engaged by pressing the ejection mechanism into the lancing device.

10. The method of ejecting a lancet from a lancing device of claim 8, wherein the method further comprises translationally mounting the ejection mechanism along the surface of the lancing device and engaging the ejection mechanism by moving the ejection mechanism along the surface of the lancing device.

* * * * *